(12) United States Patent
Bacher et al.

(10) Patent No.: US 8,617,202 B2
(45) Date of Patent: Dec. 31, 2013

(54) MEDICAL TUBULAR SHAFT INSTRUMENT AND METHOD FOR PRODUCING A FORCE TRANSMISSION ELEMENT OF THE SAME

(75) Inventors: Uwe Bacher, Tuttlingen (DE); Stefan Wittner, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 0 days.

(21) Appl. No.: 13/469,772

(22) Filed: May 11, 2012

(65) Prior Publication Data

US 2012/0290000 A1 Nov. 15, 2012

(30) Foreign Application Priority Data

May 13, 2011 (DE) .......................... 10 2011 075 785

(51) Int. Cl.
*A61B 17/00* (2006.01)
(52) U.S. Cl.
USPC ..................................................... 606/205
(58) Field of Classification Search
USPC ............ 606/170, 171, 184, 205–209; 29/434, 29/592
See application file for complete search history.

(56) References Cited

U.S. PATENT DOCUMENTS

| | | | |
|---|---|---|---|
| 5,389,104 A | 2/1995 | Hahnen et al. | |
| 5,395,375 A | 3/1995 | Turkel et al. | |
| 5,569,298 A | 10/1996 | Schnell | |
| 2002/0165538 A1 | 11/2002 | Schneiter | |

FOREIGN PATENT DOCUMENTS

| | | |
|---|---|---|
| DE | 19853305 C1 | 10/2000 |
| DE | 19855968 C1 | 10/2000 |
| DE | 20007009713 U1 | 9/2007 |

OTHER PUBLICATIONS

German Search Report; Application No. DE 10 2011 075 785.6; Issued: Mar. 16, 2012; 5 pages.
European Search Report; Application No. EP 12 00 3420; Issued: Aug. 13, 2012; 6 pages.

*Primary Examiner* — Ryan Severson
*Assistant Examiner* — Katherine M Shi
(74) *Attorney, Agent, or Firm* — St. Onge Steward Johnston & Reens LLC

(57) ABSTRACT

A medical tubular shaft instrument having a tube and a force transmission element extending lengthwise through the tube. The tube includes a jaw member arrangement on a distal end, which is coupled with the force transmission element and actuated by sliding the force transmission element along the tube. The tube includes a handpiece on a proximal end. The force transmission element, over part of its length, has a smaller outer diameter than the inner diameter of the tube to configure a ring-shaped flushing canal, and, one section along its length, it is centered in the tube in this section. The force transmission element includes precisely one section in which it is centered in the tube, and the section is in the vicinity of the distal end of the force transmission element and is perpendicular to its longitudinal axis by reshaping the force transmission element.

10 Claims, 2 Drawing Sheets

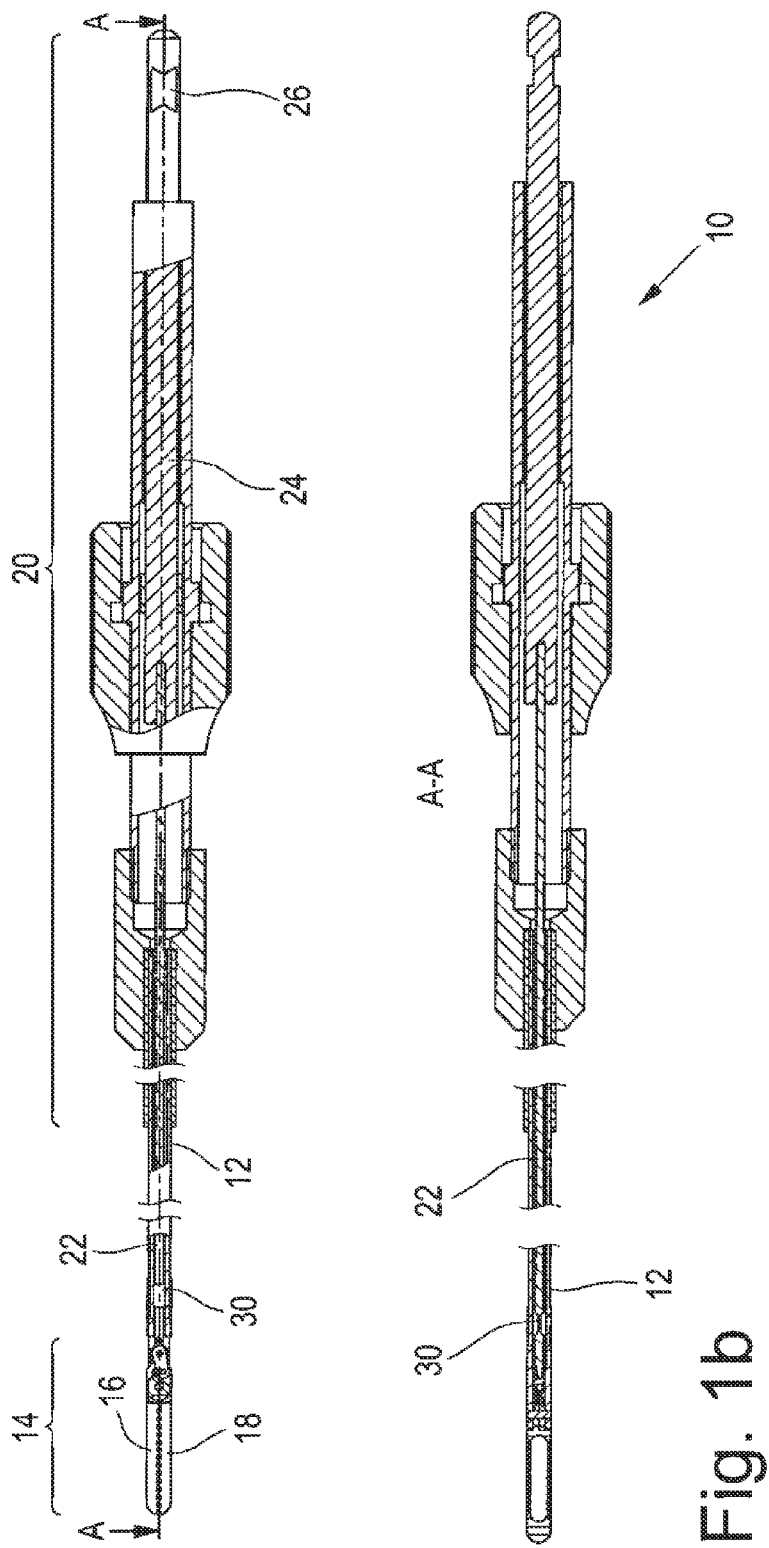

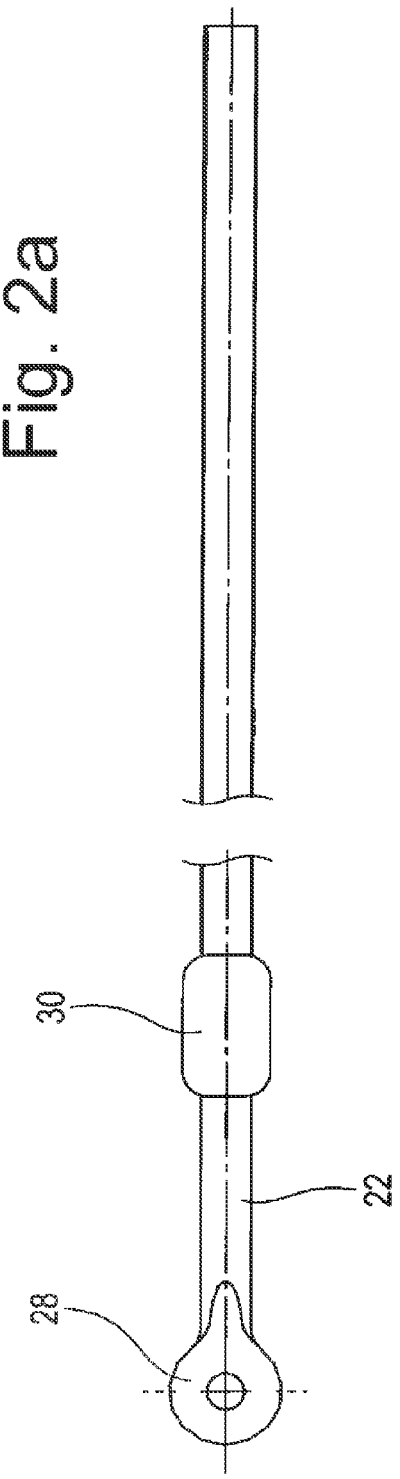
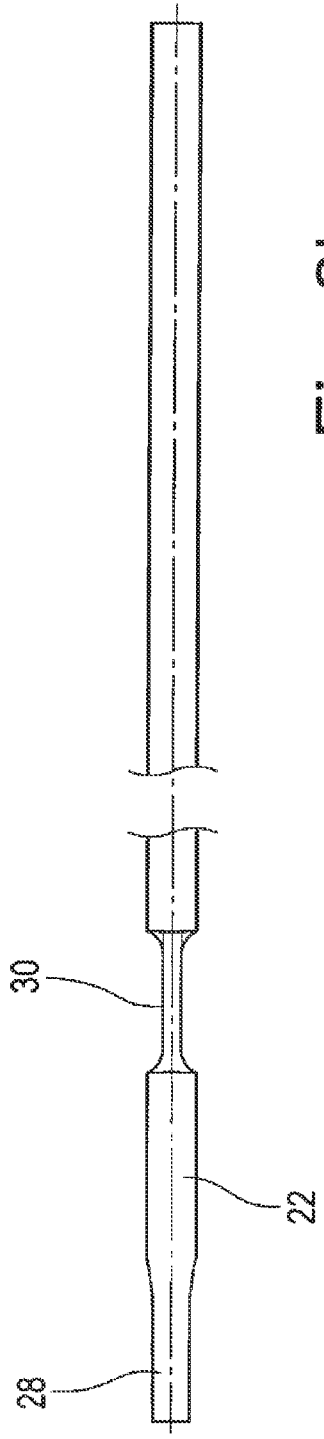
Fig. 2a
Fig. 2b

MEDICAL TUBULAR SHAFT INSTRUMENT AND METHOD FOR PRODUCING A FORCE TRANSMISSION ELEMENT OF THE SAME

CROSS-REFERENCE TO RELATED APPLICATIONS

The present application claims priority of German patent application No. 10 2011 075 785.6 filed on May 13, 2011, the content of which is incorporated herein by reference.

FIELD OF THE INVENTION

The invention relates to a medical tubular shaft instrument and a method for producing a force transmission element of a medical tubular shaft instrument. A medical tubular shaft instrument of this type and a similar production method are known from patent DE 198 55 968 C1.

BACKGROUND OF THE INVENTION

Tubular shaft instruments of this type are used as surgical instruments in minimally invasive surgery in order to perform surgical interventions through a small body incision under endoscopic control. For various surgical procedures that are to be performed in the human or animal body, such tubular shaft instruments are equipped for various functions.

A tubular shaft instrument, in the sense of the present invention, is understood to mean, for example, a forceps for cutting and/or grasping and/or a needle holder. The jaw member arrangement can have a movable jaw member that interacts with a blade of a second jaw member that is fastened to the tube. The jaw member arrangement can also have blunted jaw members for gripping tissue. In the case of a needle holder, the jaw members are suited for removably holding a needle in order to produce a seam in the surgical area to mend tissue.

To activate the jaw member arrangement, there is on the proximal end of the tube a hand piece that has a force-locked connection with the movable jaw member by means of an elongated force transmission element, normally in the form of a pull rod. Manual actuation of the handles of the hand piece causes a movement of the jaw member arrangement on the distal end of the tube in order to perform the desired task such as, for example, cutting or holding tissue or guiding a needle through the tissue.

For minimally invasive surgery, especially in operating on small children or else with procedures in certain surgical areas such as the head area, it is also necessary to configure such tubular instruments with a very small tube diameter.

In addition, with tubular shaft instruments there is the requirement that they should be flushable with liquid lengthwise, in order to avoid the necessity of completely dismantling them. To provide the space necessary for flushing, it is proposed in the aforementioned state of the art to make the pull rod generally slightly thinner than the inner diameter of the tube, but in at least one section along their length to provide three supporting protrusions, distributed around the radius, that on the one hand would support the force transmission element centrally in the tube so that it cannot easily bend, and on the other hand would also allow free space in these sections for rinsing the tube in order to comply with sterility and hygienic requirements.

SUMMARY OF THE INVENTION

It is the object of the present invention to improve the known tubular shaft instrument, on the one hand, in order to make it especially simple to produce and sufficiently stable and, on the other hand, so that it can fulfill especially strict sterility and hygienic requirements.

This object is achieved by means of a medical tubular shaft instrument having a straight elongated tube and having a rod-shaped force transmission element that extends lengthwise through the tube and can be slid along the length of the tube, such that the tube bears on a distal end a jaw member arrangement, which in addition is coupled with the force transmission element in order to be actuated by sliding the force transmission element along the tube, such that the tube on a proximal end is attached on a handpiece with hasps that can move toward one another or is set up to be attached on a handpiece of this type in such a way that the force transmission element is slid along the tube when the handpiece is manually actuated, such that the force transmission element over the greatest part of its length has a smaller outer diameter than the inner diameter of the tube in order to configure a ring-shaped flushing canal between the force transmission element and the tube and such that the force transmission element in at least one section is configured along its length in such as way that it is centered in this section in the tube and in addition free space remains for flushing out the tube with the force transmission element built in, characterized in that the force transmission element has precisely one section in which it is centered in the tube and that this section is positioned in the vicinity of the distal end of the force transmission element and that this section is configured perpendicular to its longitudinal axis by reshaping the force transmission element.

This object is also achieved by means of a method for producing a rod-shaped force transmission element of a medical tubular shaft instrument, having a straight elongated tube that bears on a distal end a jaw member arrangement and that on a proximal end is attached or attachable on a handpiece configured for manual actuation, such that the force transmission element forms a mechanical linkage, running lengthwise and with a free space through the tube, between the handpiece and the jaw member arrangement and is essentially produced of rod material that does not remove material, characterized in that the force transmission element is provided with a section for centering the force transmission element in the tube, while the force transmission element in the vicinity of its distal end is pressed flat against a level plate whose width perpendicular to the longitudinal direction of the force transmission element corresponds to the inner diameter of the tube.

The invention is based, first, on the recognition that it is sufficient to have only one section in which the force transmission element is centered in the tube, if this section is positioned in the vicinity of the distal end of the force transmission element. It has been shown that, as a rule, transverse forces that would be capable of bending the force transmission element occur only on the distal end, so that a support in this area is sufficient.

Second, the invention makes it possible, in an especially simple way, to produce the section in which the force transmission element is centered in the tube, namely by partial reshaping of the force transmission element perpendicular to its longitudinal axis, that is, through a simple pressing process.

On the contrary, in the aforementioned state of the art there are indications of how to produce supporting protrusions on the force transmission element either by expensive material removal or by rolling or pulling a round piece. In the latter case, the cross-section surface is changed because the material is stretched in the process. This also changes the streaming cross-section over the length of the force transmission element, which is detrimental to the efficiency of the flushing because the streaming speed varies throughout the length.

On the other hand, in the inventive force transmission element it is easy to ensure that the transitions between the section in which the force transmission element is centered in the tube and the other force transmission element are gentle, that is, not abrupt, and that the cross-section surface of the force transmission element that is measured crosswise to its longitudinal axis is approximately constant over its entire length. Thus the streaming cross-section is also approximately constant overall, so that with a given flushing pressure a maximum flow rate can be achieved along with maximum flushing efficiency. And because the section in which the force transmission element is centered in the tube is not mechanically weakened by any sorts of cross-section changes or abrupt transitions, the force transmission element can be produced with the minimum cross-section surface that still suffices for adequate firmness over its entire length, so that a maximum flushing cross-section can be maintained throughout.

The section in which the force transmission element is centered in the tube can contain three or more supporting protrusions that point outward, that is, are cross-shaped in arrangement.

However, in an embodiment that is preferred because especially simple to produce, there are only two supporting protrusions that are opposite one another facing outward and that are formed by the longitudinally running edges of a level plate against which the force transmission element in the section is pressed flat.

If the jaw member arrangement includes two jaw members, of which at least one is mounted so that it can pivot around a pivot axis on the distal end of the tube, then the plate-shaped force transmission element is advantageously positioned in such a way that its plane runs perpendicular to the pivot axis. In this case any possible transverse forces act on the force transmission element essentially only perpendicular to the pivot axis and only in this area, and these transverse forces are well transmitted to the tube by the correspondingly positioned plate, without the force transmission element being able to bend.

In a practical embodiment, the level plate has approximately the shape of a flat rectangular solid whose thickness is equal to about one-third to one-half of the diameter of the force transmission element and whose length in the longitudinal direction of the force transmission element is equal to approximately or at least twice the general diameter of the force transmission element.

The edges of the plate or otherwise shaped supporting protrusions can be rounded or chamfered in such a way that they have a concave shape with lower curvature than the curvature of the inner wall of the tube. Consequently, the supporting protrusions support themselves, not flat but rather in linear shape, on the inner wall of the tube, so that there are no dead spaces inaccessible to flushing liquid.

In a preferred embodiment, the tubular shaft instrument is a microsurgical forceps, and the force transmission element is a pull rod.

BRIEF DESCRIPTION OF THE DRAWINGS

There follows a description of an embodiment with reference to the drawings, which are as follows.

FIGS. 1a and 1b show level longitudinal sectional views, perpendicular to one another, through a forceps set of a microsurgical tubular shaft forceps, that is, without its handle piece.

FIGS. 2a and 2b show enlarged longitudinal views, perpendicular to one another, of the pull rod of the forceps set from FIGS. 1a and 1b.

DETAILED DESCRIPTION OF THE INVENTION

FIGS. 1a and 1b depict a forceps set of a microsurgical tubular shaft forceps labeled with the general reference number 10.

The forceps set 10 contains a straight elongated rigid tube 12, which bears on its distal end a jaw member arrangement 14 comprising two jaw members 16 and 18 that can pivot with respect to one another. The two jaw members 16 and 18 can be pivotable, or just one can be pivotable while the other is attached immovably on the tube 12. The jaw member arrangement 14 is depicted here as a gripping forceps, but with correspondingly configured jaw members can also be a cutting forceps.

The tube 12 is seated on its proximal end in an end of an elongated, more or less tubular-shaped retainer 20, which can be affixed on a handpiece that is not shown and that has hafts of which at least one is movable.

A pull rod 22, which runs centrally throughout the tube 12, is coupled on a distal end by tiny levers with a jaw member or with both jaw members 16, 18. At its proximal end, the pull rod 22 extends slightly further axially into the retainer 20 and is there coupled by force-locking with an additional, thicker rod 24, which extends axially through the retainer 20 and exits on its proximal end.

The other rod 24 has on its proximal end a coupling member 26 for coupling with the hafts of the handpiece. The pull rod 22 and the other rod 24 form a mechanical linkage between the jaw member arrangement 14 and the hafts of the handpiece on which the retainer 20 is attached, in order to hold the tubular shaft forceps with one hand and thereby to allow manual opening or closing of the jaw members 16 and 18, possibly against the force of a spring.

The pull rod 22, shown enlarged in FIGS. 2a and 2b, has generally a diameter that is sufficiently smaller than the inner diameter of the tube 12 so that adequate space remains for axial rinsing out of the tube 12 when the pull rod 22 is built in.

For rinsing out, the forceps set 10 is placed in a washing machine for medical instruments and is connected at one end by a hose and adapter with a fluid link-up that provides flushing liquid standing under low pressure.

As can be recognized in FIG. 2, the pull rod 22 has on its distal end a head 28 with holes for a jointed connection with the levers of the jaw members 16 or 18.

Not far removed from its distal end, the pull rod 22 is pressed flat to a level plate 30 in a section whose axial length is equal to approximately triple the general thickness of the pull rod 22. The material stressed by pressing is essentially diverted perpendicular to the longitudinal direction of the pull rod 22, to a distance so that the width of the plate 30 corresponds to the inner diameter of the tube 12, so that the pull rod 22 is fed centrally by the plate 30 in the tube 12. This means that the edges of the plate 30 running in the longitudinal direction of the tube 12 form corresponding supporting elements.

By means of a suitable punch, another supporting structure could be produced in similar manner, for example with supporting elements positioned in a triangular or star-shaped manner.

In the illustrated embodiment, the pull rod 22 is generally 4 mm thick and the plate 30 is approximately 11 mm long, 1.15 mm thick and 7 mm wide, so that its width is adapted to a tube with a 7 mm inner diameter; that is, it can be slightly smaller. The result of these dimensions is that the plate 30 has almost the same cross-section area perpendicular to the longitudinal direction as the pull rod 22. A small difference is harmless and can be due to a material-removing impact on the edges of the plate 30 and/or a small material stretching in the longitudinal direction from pressing.

As can be recognized in FIGS. 1a and 1b, the plane of the plate 30 is perpendicular to the pivot axis of the jaw members 16, 18 of the jaw member arrangement 14. Thus the plate 30 supports the pull rod 22 in the optimal direction, and precisely in the direction in which transverse forces occur soonest, in the inner wall of the tube 12.

Although not shown in the drawings, the edges of the plate 30 can be set up perpendicular to the longitudinal direction of the pull rod 22 with roundings or chamfers in order to produce a concave shape with lower curvature than the curvature of the inner wall of the tube 12, so that the plate 30 is supported only linearly and not more or less flatly on the inner wall of the tube 12.

The invention claimed is:

1. A medical tubular shaft instrument, comprising:
   a straight elongated tube having a proximal and distal end; and
   a rod-shaped force transmission element that extends lengthwise through the tube and is slidable along the length of the tube, said rod-shaped force transmission element having a plurality of sections;
   such that the tube bears on its distal end a jaw member arrangement, which in addition is coupled with the force transmission element in order to be actuated by sliding the force transmission element along the tube,
   such that the tube on its proximal end is attached on a handpiece with hasps that can move toward one another or the tube is set up to be attached on a handpiece of this type in such a way that the force transmission element is slid along the tube when the handpiece is manually actuated,
   such that the force transmission element over a majority of its length has a smaller outer diameter than the inner diameter of the tube in order to configure a ring-shaped flushing canal between the force transmission element and the tube and
   such that the force transmission element in one section is configured along its length in such a way that it is centered in this section in the tube and in addition free space remains for flushing out the tube with the force transmission element disposed within,
   characterized in that
   the force transmission element has precisely one section in which it is centered in the tube and that this section is positioned in the vicinity of the distal end of the force transmission element and that this section is extends perpendicularly to its longitudinal axis by reshaping the force transmission element.

2. The medical tubular shaft instrument according to claim 1, wherein transitions between the section in which the force transmission element is centered in the tube and the remaining sections of the force transmission element are tapered, and a surface of the force transmission element that is measured crosswise to the longitudinal axis of the force transmission element is approximately constant over its entire length.

3. The medical tubular shaft instrument according to claim 2, wherein the section in which the force transmission element is centered in the tube contains three or more supporting protrusions that point radially outward.

4. The medical tubular shaft instrument according to claim 1, wherein the section in which the force transmission element is centered in the tube contains three or more supporting protrusions that point radially outward.

5. The medical tubular shaft instrument according to claim 1, wherein the section in which the force transmission element is centered in the tube contains precisely two supporting protrusions, said two supporting protrusions are positioned opposite one another pointing outward and are formed by longitudinally running edges of a level plate formed by pressing the section of the force transmission element flat.

6. The medical tubular shaft instrument according to claim 5, wherein the jaw member arrangement includes two jaw members of which at least one is mounted so that it can pivot on the distal end of the tube around an axis that runs perpendicular to the plane of the plate of the force transmission element.

7. The medical tubular shaft instrument according to claim 6, wherein the plate has approximately the shape of a flat rectangular solid whose thickness is equal to about one-third to one-half of the diameter of the force transmission element and whose length in the longitudinal direction of the force transmission element is equal to approximately or at least twice the general diameter of the force transmission element.

8. The medical tubular shaft instrument according to claim 5, wherein the plate has approximately the shape of a flat rectangular solid whose thickness is equal to about one-third to one-half of the diameter of the force transmission element and whose length in the longitudinal direction of the force transmission element is equal to approximately or at least twice the general diameter of the force transmission element.

9. A medical tubular shaft instrument according to claim 5 wherein the supporting protrusions are shaped in such a way that their contact areas with the inner wall of the tube are linear in shape.

10. A medical tubular shaft instrument according to claim 1, wherein the instrument is a microsurgical forceps and the force transmission element is a pull rod.

* * * * *